United States Patent [19]
Clark et al.

[11] Patent Number: 6,090,041
[45] Date of Patent: Jul. 18, 2000

[54] VACUUM ACTUATED SURGICAL RETRACTOR AND METHODS

[75] Inventors: Orlo H. Clark, San Francisco; Arthur M. Moran, San Bruno, both of Calif.

[73] Assignee: Regents of the University of California, Oakland, Calif.

[21] Appl. No.: 09/246,987

[22] Filed: Feb. 16, 1999

[51] Int. Cl.[7] .................................................. A61B 17/00
[52] U.S. Cl. .......................................... 600/205; 600/206
[58] Field of Search ..................................... 600/201, 204, 600/205, 210, 235, 37; 606/1, 115, 113, 114, 167; 600/104, 126, 156, 159, 206

[56] References Cited

U.S. PATENT DOCUMENTS

| | | | |
|---|---|---|---|
| 2,082,782 | 6/1937 | Allen | 600/205 |
| 2,482,116 | 9/1949 | Lanahan | 600/205 |
| 4,047,532 | 9/1977 | Phillips et al. | |
| 5,342,385 | 8/1994 | Norelli et al. | 606/193 |
| 5,423,830 | 6/1995 | Schneebaum et al. | 606/127 X |
| 5,450,842 | 9/1995 | Tovey et al. | 600/206 |
| 5,762,606 | 6/1998 | Minnich | 600/205 |
| 5,810,806 | 9/1998 | Richart et al. | 606/45 |
| 5,865,730 | 2/1999 | Fox et al. | 600/201 X |
| 5,865,827 | 2/1999 | Bullister | 606/1 |

*Primary Examiner*—Jeffrey A. Smith
*Attorney, Agent, or Firm*—Lumen Intellectual Property Services

[57] ABSTRACT

A vacuum actuated surgical retractor for retracting body tissue or organs comprises an end-piece adapted for sealing engagement with body tissue, the end-piece having at least one suction port therein, the at least one suction port operably linked to at least one vacuum line. Suction supplied to the at least one suction port may be controlled by a vacuum control unit. Retractors of the invention may be provided in a range of shapes and sizes according to the intended application or tissue to be retracted. A method for making a vacuum actuated retractor of the invention is disclosed, together with a method for atraumatically retracting body tissue.

45 Claims, 18 Drawing Sheets

VACUUM ACTUATED SURGICAL RETRACTOR AND METHODS

BACKGROUND OF THE INVENTION

1. Field of the Invention

This invention relates to a vacuum actuated surgical retractor. In particular, this invention relates to a surgical retractor for atraumatically retracting target tissue or an organ of a patient, wherein the retractor uses suctional force applied to the tissue or organ to effect retraction. This invention further relates to a method of making a vacuum actuated surgical retractor, and to a method of retracting, in an atraumatic manner, body tissue or an organ using a vacuum actuated retractor.

2. Background of the Related Art SF99-024

Retraction of various tissues or organs is commonly performed during many surgical procedures. Prior art retractors generally have jaws or arms for grasping tissue or organs—typically various types of forceps for open procedures, and fan-or claw-like retractors currently used in videoscopic operations. Such prior art retractors normally have rigid, hard, and/or sharp components which make contact with tissues, and can traumatize or damage the tissue or organ to be retracted. Thus, using conventional apparatus and methods for retracting tissue or organs, bleeding and other forms of fluid or tissue leakage from the target tissue or organ may ensue, either during or after retraction.

U.S. Pat. No. 5,810,806 to Ritchart et al. discloses methods and devices for the collection of tissue samples. The device includes a tubular body having a proximal end and a distal end, an electrosurgical cutting element, and a primary lumen for receiving a tissue sample. A means for drawing (e.g., a vacuum) tissue samples into the primary lumen is also provided.

U.S. Pat. No. 5,450,842 to Tovey discloses a surgical retractor including a rod member having a preformed configuration, the rod member movable between a deformed configuration and the preformed configuration.

U.S. Pat. No. 5,342,385 to Norelli, et al. discloses a surgical retractor including a generally annular bladder. The bladder may be inserted in an incision or orifice, and inflated to exert an outward radial force against surrounding tissue.

A Malstrom retractor is a prior art device useful in the delivery of babies when they fail to descend into the birth canal in the normal manner. A suction cup of the Malstrom device is applied to the head of the baby to allow the surgeon to pull on the baby.

The instant invention provides a vacuum actuated surgical retractor which allows the surgeon to atraumatically retract tissue, e.g. malignant or benign tumors, and normal organs. The retractor may be used for both conventional and videoscopic surgical procedures. The retractor of the invention relies on the application by the retractor of a suction force on, for example, the capsule of a tumor or organ to be retracted, as will be described fully hereinbelow. The retractor of the invention features soft, pliable components adapted for contacting the target tissue or organ. Therefore, the retractor of the invention is less likely to injure normal organs or to fracture the capsule of tumors, as compared with prior art surgical retractors. In addition, the retractor of the invention allows operations to be performed more easily and efficiently, through smaller incisions, and in less time, as compared with prior art devices and procedures.

SUMMARY OF THE INVENTION

The surgical retractor of the invention relies on the principle of applying suction to the surface of an organ or tissue to be retracted. Suction is applied to the target tissue or organ via at least one relatively soft, pliable component which may conform to the shape of the target. The suction applied to the target may be controlled, e.g., by a vacuum control unit. Retraction in this manner, using a suction force which may be distributed over a relatively large surface area of the target tissue or organ, is atraumatic and causes minimal damage, if any. The use of suction for surgical retraction has the additional advantage of serving to prevent or restrict fluid or tissue leakage or escape, e.g., from a tumor, during an operation. Retractors of different sizes and shapes may be provided, e.g., according to the size and/or shape of a tumor or organ to be retracted. An embodiment of the invention suitable for videoscopic applications may feature one or more components of the vacuum actuated retractor which are foldable and/or compressible in order to permit or facilitate advancement of the instrument through a sleeve, catheter, or the like.

An object, therefore, of the invention is to provide a vacuum actuated surgical retractor for retraction of an organ, tumor, or other tissue.

Another object of the invention is to provide a method of retracting an organ or tissue by the application of suction to the organ or tissue.

One advantage of the invention is that it provides a surgical retractor which uses suction force to retract a target tissue or organ, with minimal or no damage being sustained to the target tissue or organ.

Another advantage of the invention is that it provides a surgical retractor which may be introduced into a patient via a small incision, a cannula, or a catheter.

Another advantage of the invention is that it provides a vacuum actuated retractor which can be used for atraumatic retraction of a tumor or organ, wherein only a portion of the tumor or organ needs to be exposed for retraction to proceed.

Another advantage of the invention is that it provides a vacuum actuated surgical retractor which may include an instrument port for manipulating an instrument therethrough, for excision of target tissue, or for the delivery of a therapeutic agent thereto.

Another advantage of the invention is that it provides a vacuum actuated surgical retractor including a soft, pliable end-piece adapted for making sealing engagement with a target tissue or organ.

Another advantage of the invention is that it provides a vacuum actuated surgical retractor including an end-piece having at least one suction port therein.

Another advantage of the invention is that it provides a vacuum actuated surgical retractor including at least one vacuum control unit for controlling suction to the end-piece of the retractor.

Another advantage of the invention is that it prevents or minimizes the release of cells from target tissue into adjacent, non-target tissue during tissue excision or biopsy procedures.

Another advantage of the invention is that it provides a method for atraumatic retraction of an organ or tissue, including the application of suction to the surface of the organ or tissue.

Another advantage of the invention is that it provides a method of making a vacuum actuated surgical retractor apparatus and system.

One feature of the invention is that it utilizes suction for surgical retraction of body tissue or an organ.

Another feature of the invention is that it causes minimal or no damage to target tissue being retracted.

Another feature of the invention is that it can be used for videoscopic, laparoscopic, or endoscopic surgical procedures.

Another feature of the invention is that it provides a convenient and efficient method for atraumatic surgical retraction of a tumor, an organ, or tissue.

These and other objects, advantages and features are accomplished by the provision of a surgical retractor for retracting body tissue, including a head unit having an end-piece, the end-piece having at least one suction port therein. The end-piece is connected to a vacuum supply unit. The vacuum supply unit and end-piece are adapted for supplying suction to the at least one suction port. The end-piece and at least one suction port are adapted for making sealing engagement with body tissue, such as the capsule of a tumor or an organ.

These and other objects, advantages and features are accomplished by the provision of a vacuum actuated surgical retractor system for retraction of body tissue, such as an organ, a tumor, etc., the system including: a retractor including an end-piece adapted for sealing engagement against body tissue, wherein the end-piece includes at least one suction port for exerting a suction force on the body tissue; a vacuum supply unit operably linked to the end-piece for supplying suction to the at least one suction port; and a vacuum control unit for controlling suction to the at least one suction port.

These and other objects, advantages and features are accomplished by the provision of a method for atraumatic retraction of body tissue using a vacuum actuated surgical retractor, the method including the steps of: a) placing an end-piece of the surgical retractor against the body tissue, the end-piece having at least one suction port; and b) supplying suction to the at least one suction port such that a suction force is exerted on the body tissue via the end-piece.

These and other objects, advantages and features of the invention will be set forth in part in the description which follows and in part will become apparent to those having ordinary skill in the art upon examination of the following or may be learned from practice of the invention. The advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The instant invention provides a surgical retractor which is relatively simple in its design and operation, and which can be used by a surgeon for atraumatically retracting body tissues. Unless otherwise stated, the term "tissue" as used herein may include a malignant tumor, a benign tumor, colonic polyps, cysts, a normal organ (such as the eye, the liver, the kidneys, etc.), an organ having a tumor associated therewith, or any other normal or abnormal body tissue. The retractor of the invention may also be used to retract, recover, or retrieve an inanimate object purposely or inadvertently introduced into the body or a body cavity of an individual or patient.

Figure 1A:
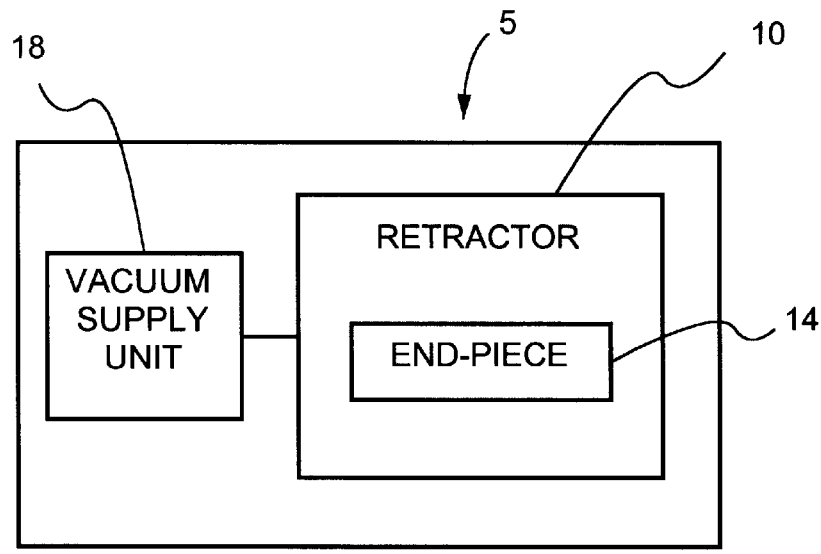
FIG. 1A is a block diagram schematically representing a surgical retractor system, according to one embodiment of the invention.

Referring now to the drawings, FIG. 1A shows a block diagram representing a vacuum actuated surgical retractor system 5, according to one embodiment of the instant invention. System 5 includes a vacuum actuated surgical retractor 10 having an end-piece 14 functionally coupled to a vacuum supply unit 18. A vacuum control unit 16/16' (FIGS. 2A, 2B) may be operably linked to vacuum supply unit 18 and/or retractor 10, according to various embodiments of the invention.

Figure 1B:
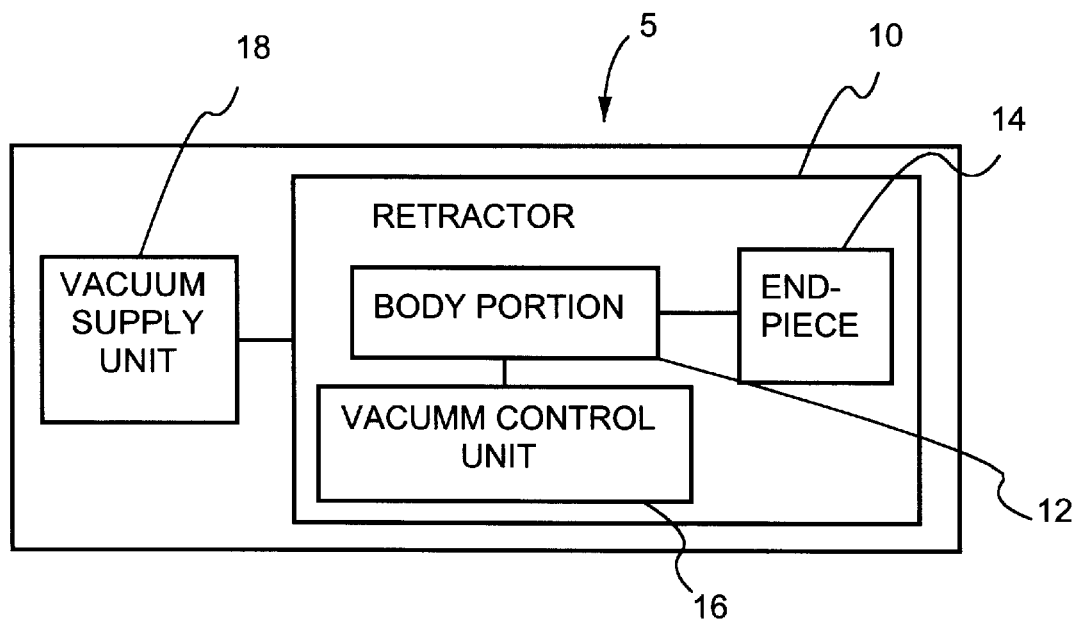
FIG. 1B is a block diagram schematically representing a surgical retractor system, according to another embodiment of the invention.

FIG. 1B schematically represents surgical retractor system 5, according to another embodiment of the invention, in which retractor 10 includes a body portion 12 functionally coupled to end-piece 14. End-piece 14 is functionally coupled to vacuum supply unit 18. A vacuum control unit 16 is operably linked to body portion 12 for controlling suction or vacuum from vacuum supply unit 18 delivered to end-piece 14. Vacuum control unit 16 may control suction or vacuum delivered to end-piece 14 qualitatively and/or quantitatively. That is to say, vacuum control unit 16 may be adapted to turn on or off unit 18, and/or to control the magnitude of a suction force at end-piece 14. In the latter case, the magnitude of a suction force at end-piece 14 may be controlled directly by interacting with vacuum supply unit 18, or by interacting with one or more components of retractor 10. For example, vacuum control unit 16 may comprise a valve (not shown) coupled to body portion 12 for controlling or adjusting the magnitude of a suction force at end-piece 14. Devices and techniques for controlling and/or adjusting suction or vacuum are well known in the art, and may be used in conjunction with the instant invention.

Figure 2A:
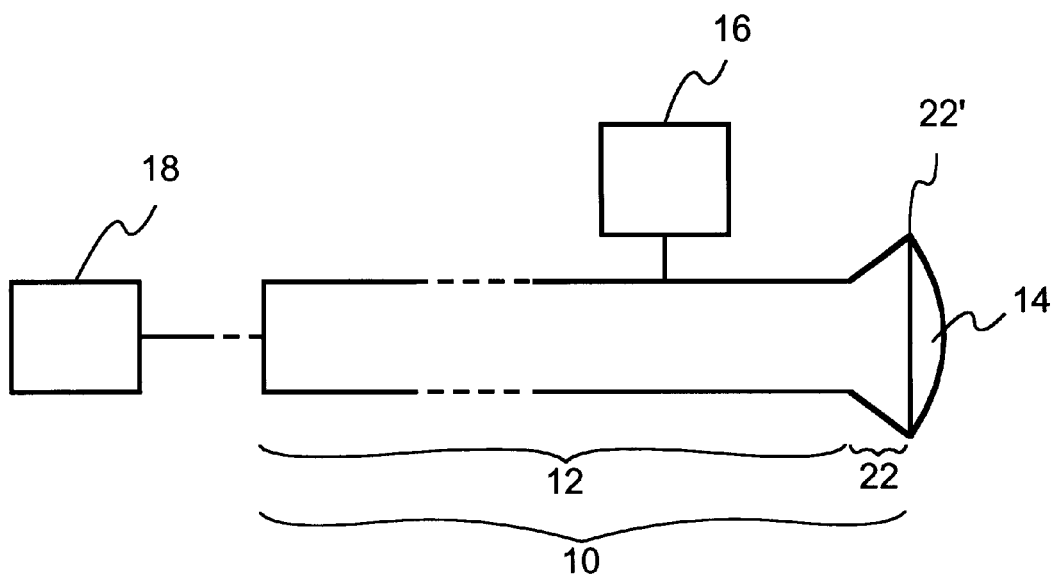
FIG. 2A schematically represents a surgical retractor system, according to another embodiment of the invention.

FIG. 2A schematically represents surgical retractor system 5, according to the instant invention, including retractor 10 coupled to vacuum supply unit 18, with retractor 10 viewed laterally. Retractor 10 includes body portion 12, end-piece 14, vacuum control unit 16, and a head unit 22. Head unit 22 includes head distal end 22'. According to the embodiment of FIG. 2A, vacuum control unit 16 is integral with retractor 10. According to a currently preferred embodiment, vacuum control unit 16 is attached to body portion 12. Vacuum control unit 16 may comprise a hole, a valve, (neither of which are shown), or other device known in the art for controlling the flow of air or gases. Vacuum control unit 16 may be easily operated, e.g., using one or more digits of a hand of the surgeon.

Figure 2B:
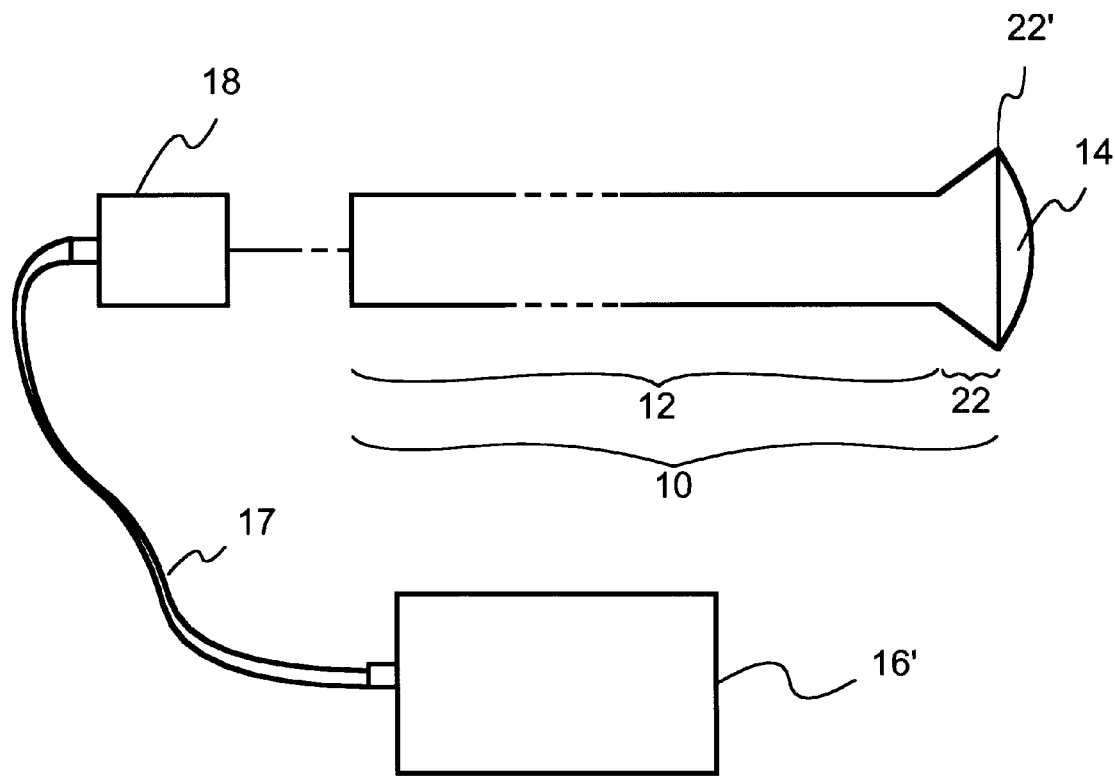
FIG. 2B schematically represents a surgical retractor system, according to another embodiment of the invention.

FIG. 2B represents surgical retractor system 5, according to another embodiment of the instant invention, again including retractor 10 coupled to vacuum supply unit 18, with retractor 10 viewed laterally, as for FIG. 2A. According to the embodiment of FIG. 2B, a non-integral vacuum control unit 16' is coupled directly to vacuum supply unit 18 via connector 17 for controlling vacuum or suction provided by vacuum supply unit 18 to end-piece 14. Unit 16' may be adapted for qualitative and/or quantitative control suction or vacuum provided to end-piece 14.

As an example only, and not to limit the invention in any way, vacuum supply unit 18 may be a compressor or vacuum pump, and unit 16' may be a variable speed foot pedal (analogous to the gas pedal of a conventional automobile) for controlling the speed or power of vacuum supply unit 18 over a range from zero (OFF) to maximum. Conventional wireless communication techniques well known in the art, e.g., using a transmitter/receiver system operating at various wavelengths of electromagnetic radiation, may optionally be employed in lieu of, or in addition to, connector 17.

Figure 3:
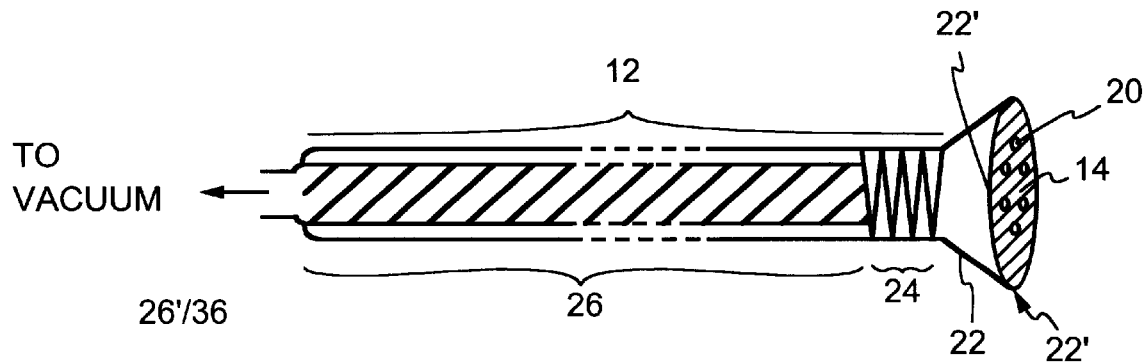
FIG. 3 shows a schematic representation of a surgical retractor, according to one embodiment of the invention.

FIG. 3 shows surgical retractor 10, having a generally frusto-conical head unit 22 and elongated body 12 comprising a shaft 26 and a neck portion 24, according to one embodiment of the invention. Head unit 22 includes head distal end 22'. End-piece 14 is sealingly attached to head unit 22 at or near head distal end 22', such that substantially no air flows between the periphery of end-piece 14 and the edges of head distal end 22'. As a result, airflow through one or more suction ports 20 may be more readily controlled. End-piece 14 preferably comprises a soft and/or pliable material, also preferably having a fairly smooth surface, such as various natural or synthetic rubber or rubber-like materials well known in the art, e.g., silicone rubber, and neoprene.

End-piece 14 includes one or more suction ports 20. Suction ports 20 are in communication with vacuum supply unit 18 via one or more vacuum lines 36 (FIGS. 9A, 9C, 10A, 10B). According to one embodiment of the invention a bore 26' within shaft 26 may comprise vacuum line 36. Suction ports 20 are adapted to allow the passage of air therethrough, for example, in response to the action of vacuum supply unit 18 providing suction within vacuum line 36. Suction ports 20 are also adapted to make sealing engagement with a surface of body tissue or an organ when end-piece 14 is placed in contact with the body tissue or organ, such that a suction force is applied to the surface of the body tissue or organ when suction is supplied to end-piece 14 (e.g., by activation of unit 18).

The size, number, and arrangement of suction ports 20 on end-piece 14 may be varied according to the particular applications, for example, the size, shape, fragility, and surface characteristics of the tissue or organ to be retracted.

Retractor 10 in general, and head unit 22 in particular, may be provided in various shapes, lengths and widths for a broad range of surgical retraction applications. By way of example, only, and not to limit the invention in any way, a relatively small retractor 10 may be provided for retracting the eye or a 2 cm. diameter parathyroid tumor. A larger retractor 10 may be used to retract a normal kidney, a kidney with a tumor, an adrenal tumor, normal liver and other large tissue masses.

Neck portion 24 may be more or less flexible, allowing head unit 22 to project at various angles with respect to shaft 26. Neck portion 24 may be adapted to retain a given position, relative to shaft 26, in which neck 24 has been arranged. Thus, material comprising neck portion 24 may be characterized as possessing positional memory, such materials being well known in the art. Shaft 26 may itself be more or less flexible along at least part of its length, or may be rigid over part of its length or over its entire length.

Although retractor body portion 12 is shown in FIG. 3 as being generally cylindrical, and head unit 22 is shown as having a generally frusto-conical shape, other shapes for retractor 10 and its components are contemplated (e.g., FIGS. 7A–7C) and are within the scope of the invention.

Figure 4A:
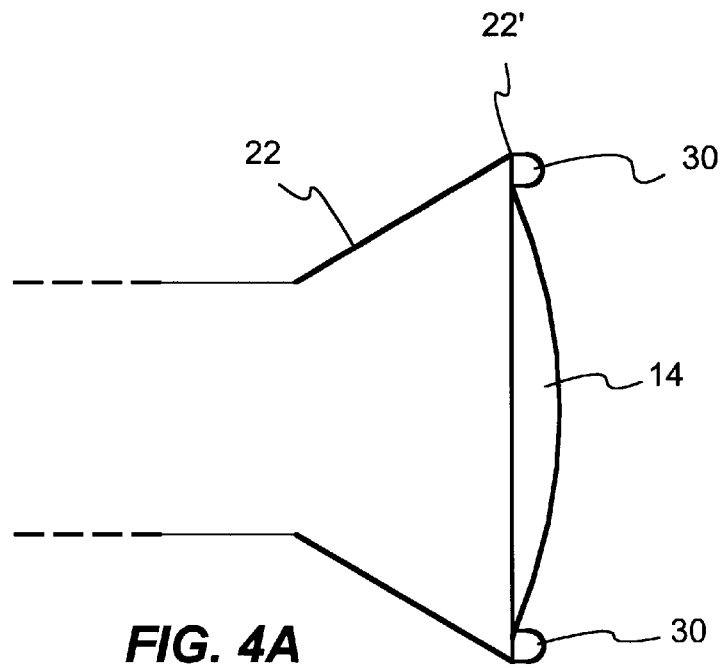
FIG. 4A is a lateral view of a head unit and end-piece of a surgical retractor showing an end-piece auxiliary sealing unit extending distally beyond the head distal end of the retractor, according to another embodiment of the invention.
Figure 4B:
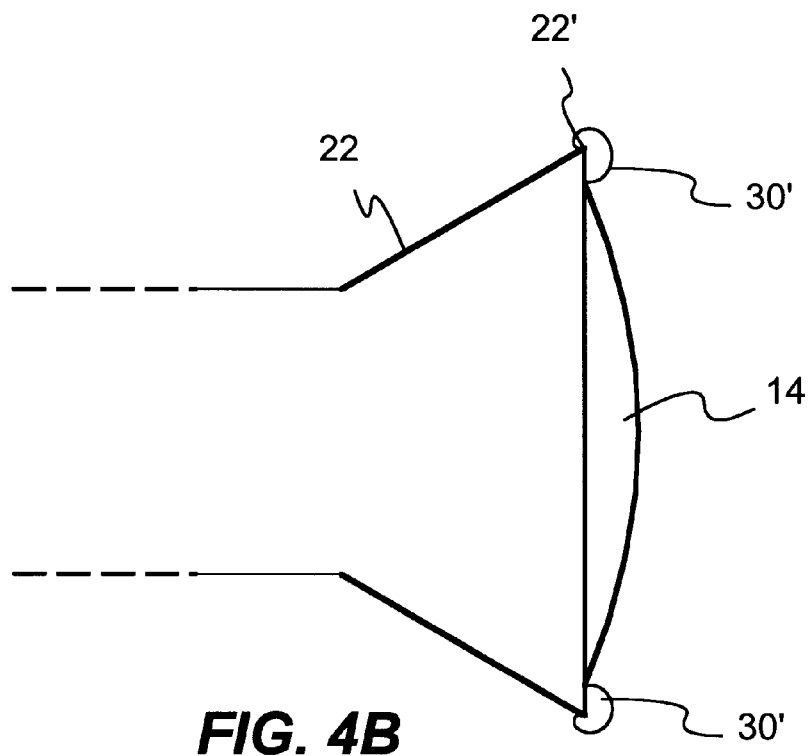
FIG. 4B is a lateral view of a head unit and end-piece of a surgical retractor showing an end-piece auxiliary sealing unit protruding distally and laterally beyond the head distal end of the retractor, according to another embodiment of the invention.

FIGS. 4A and 4B are lateral views of head unit 22, according to other embodiments of the invention, showing auxiliary sealing unit 30 (FIG. 4A) and auxiliary sealing unit 30' (FIG. 4B). Auxiliary sealing unit 30 may protrude distally to a greater or lesser extent beyond head distal end 22', while auxiliary sealing unit 30' may extend distally and/or laterally to greater or lesser extents beyond head distal end 22'. Auxiliary sealing unit 30/30' assist in making sealing engagement of end-piece 14 with tissue or an organ to be retracted. Auxiliary sealing unit 30 may comprise, for example, a natural, synthetic, or semi-synthetic, pliable and/or compressible material, preferably having a smooth exterior. Auxiliary sealing units 30/30' may be solid or hollow and pneumatic (air-filled) or gel-filled. End-piece 14 is shown as being concave with respect to distal end 22'. However, other configurations for end-piece 14 are also within the scope of the invention (see, e.g., FIGS. 5A–5C).

Figure 4C:
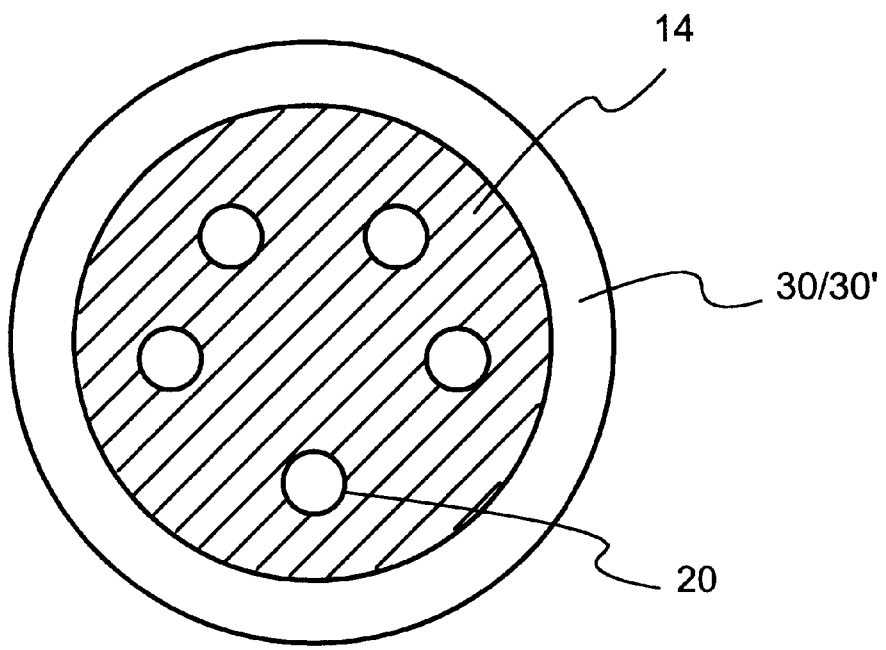
FIG. 4C is a face view of an end-piece of a surgical retractor including an auxiliary sealing unit, according to the invention.

FIG. 4C shows end-piece 14 having sealing unit 30 (30') arranged circumferentially on end-piece 14. It should be noted, however, that other arrangements for unit 30 (30') are contemplated and are within the scope of the invention. End-piece 14 of FIG. 4C shows five suction ports 20 of approximately equal size. However, as noted elsewhere herein, other numbers and arrangements of suction ports 20 are also within the scope of the invention.

Figure 5A:
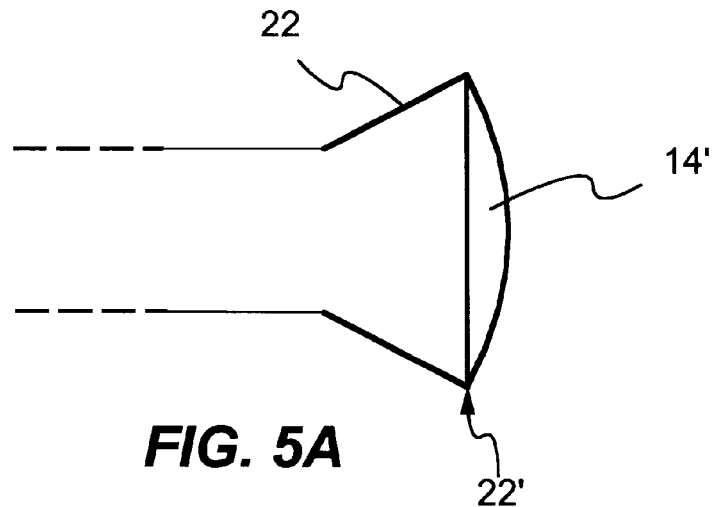
FIGS. 5A–5C each show a lateral view of a head unit and end-piece of a surgical retractor, according to embodiments of the invention.
Figure 5B:
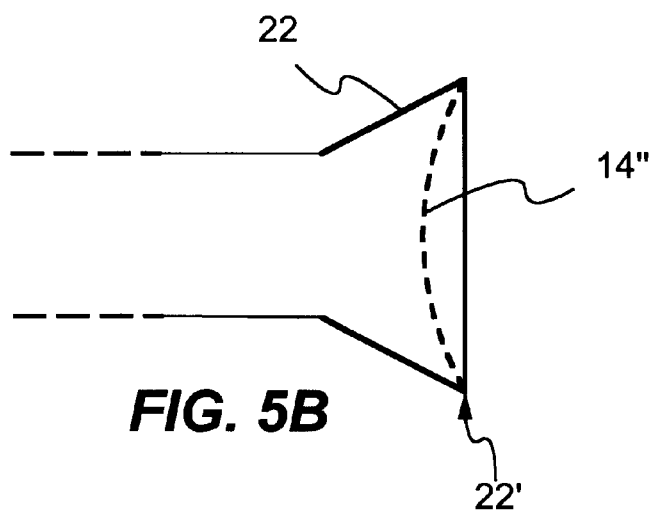

FIG. 5A is a lateral view of head unit 22 having end-piece 14' attached at or near distal end 22', wherein end-piece 14' adopts a convex shape with respect to distal end 22', according to one embodiment of the invention. End-piece 14' may comprise a pliable, elastic material which allows end-piece 14' to convert to a concave shape with respect to distal end 22', and to inter-convert between a convex shape and a concave shape, in response to the application of a force to end-piece 14'. FIG. 5B is a lateral view of head unit 22 having end-piece 14" attached at or near distal end 22', according to another embodiment of the invention, wherein end-piece 14" adopts a concave shape with respect to distal end 22'. Somewhat analogous to the situation described above with respect to FIG. 5A, end-piece 14" may convert to a convex shape with respect to distal end 22' and may be adapted to inter-convert between concave and convex, in response to the application of a force to end-piece 14". Under this embodiment of the invention, end-pieces 14' and 14" may be substantially equivalent to each other.

Figure 5C:
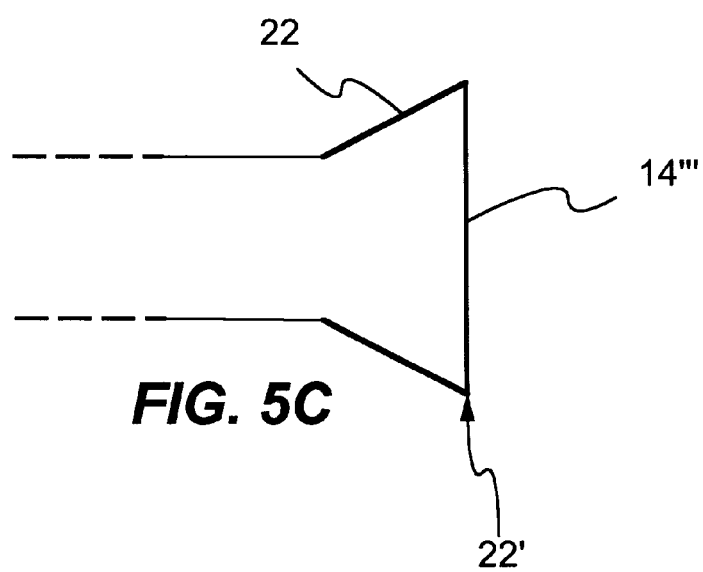

FIG. 5C is a lateral view of head unit 22 having end-piece 14'" attached at or near distal end 22', according to another embodiment of the invention, wherein end-piece 14'" is substantially planar (i.e. neither convex nor concave with respect to distal end 22'). End-piece 14'" may comprise a pliable, elastic material which allows end-piece 14'" to adopt either a concave or a convex shape with respect to distal end 22', e.g., depending on the direction of an applied force to end-piece 14'".

Figure 6A:
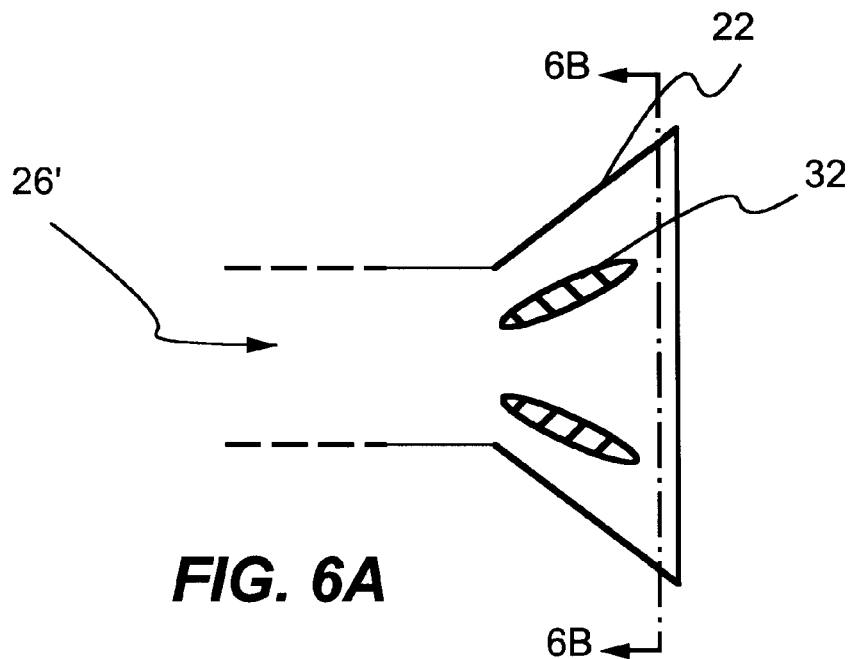
FIG. 6A is a side view of a head unit showing external head support units.
Figure 6B:
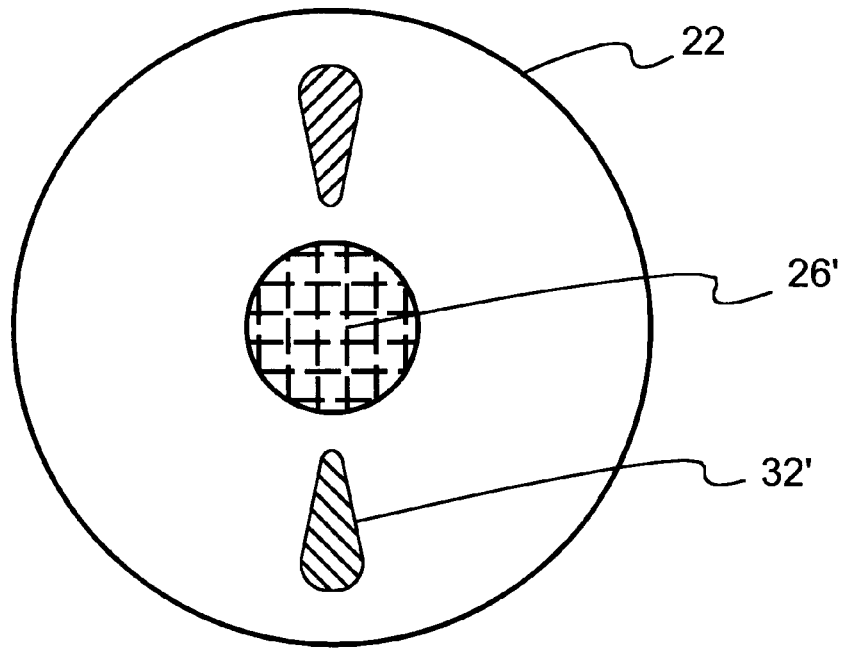
FIG. 6B is a face view of the interior of a head unit showing internal head support units, both according to the invention.

FIG. 6A shows, in side view, head unit 22 having external head support units 32 arranged on the exterior surface of head unit 22. Alternatively or in addition to external head support units 32, internal head support units 32' may be arranged internally within head unit 22, as shown in FIG. 6B. Head support units 32/32' serve to support, and provide resiliency to, head unit 22. The number, size, arrangement, and composition of support units 32/32' may be selected or designed according to the desired properties of head unit 22 and the intended application(s) of retractor 10.

Figure 7A:
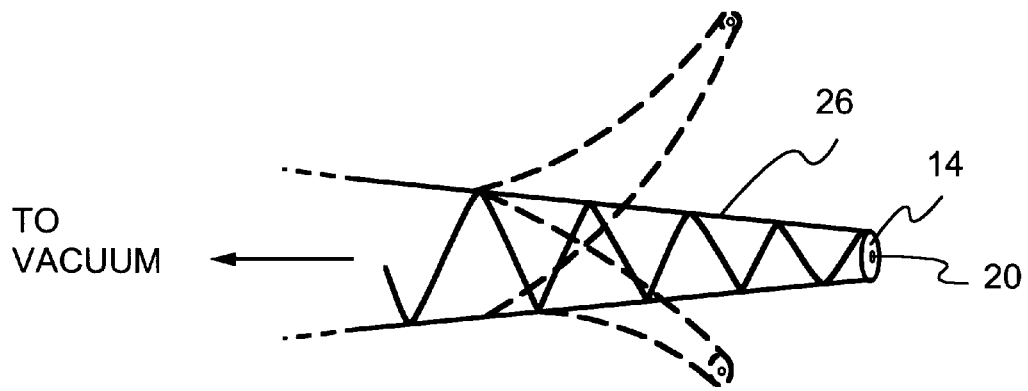
FIG. 7A shows a flexible distal portion of a retractor including an end-piece.

FIG. 7A shows the distal portion of retractor 10 having elongated shaft 26, according to another embodiment of the invention, wherein shaft 26 flexible over at least part of its length. Thus, according to certain embodiments of the invention, head unit 22 may be incorporated into the distal part of shaft 26, greatly reduced in length, vestigial, or substantially absent. Flexibility of shaft 26 allows for curvature of part or all of shaft 26 to varying extents and in a plurality of different directions, according to the particular application or use of retractor 10. End-piece 14, having at least one suction port 20, may be fitted at or near the distal end of shaft 26. The flexible nature of shaft 26 enhances the maneuverability of retractor 10 and, for certain applications, facilitates contacting of end-piece 14 with a target body tissue or organ.

Figure 7B:
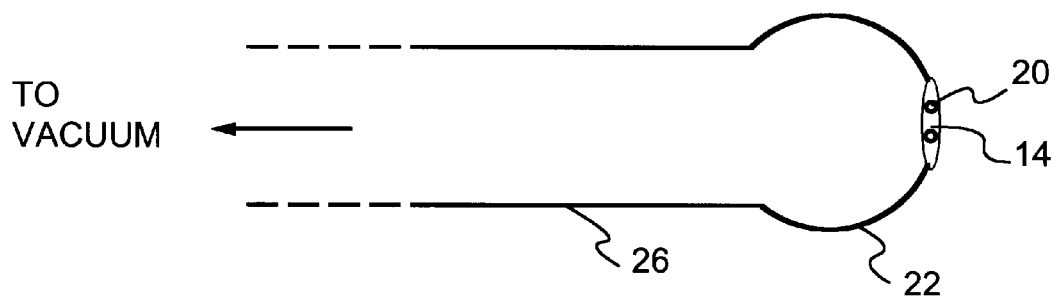
FIG. 7B shows a distal portion of a retractor having a rounded head unit.

FIG. 7B shows the distal portion of retractor 10 having a rounded head unit 22 affixed to an elongated shaft 26, according to another embodiment of the invention. End-piece 14, including at least one suction port, is attached at or near distal end 22' of head unit 22. The rounded nature of head unit 22 of the embodiment depicted in FIG. 7B may facilitate advancement of end-piece 14 towards targeted tissue or organs, while preventing damage to both target and non-target tissues or organs.

Figure 7C:
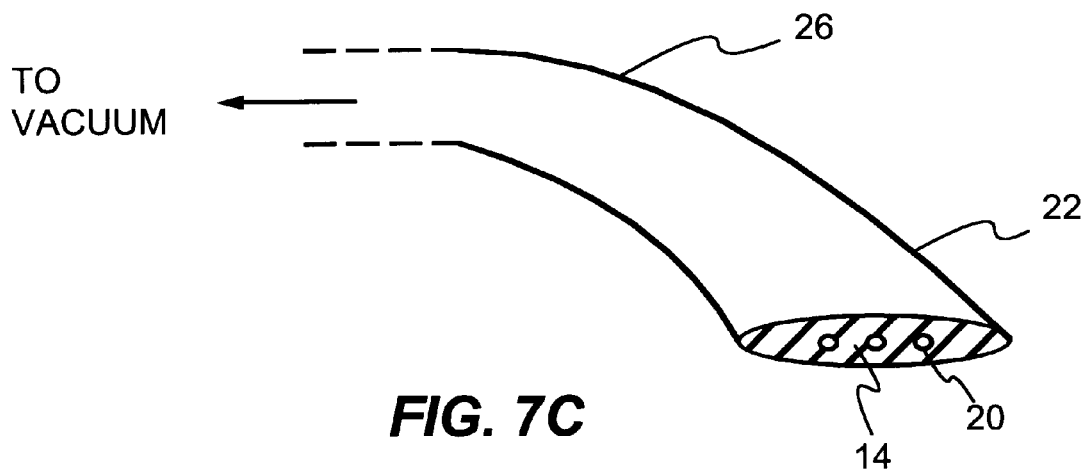
FIG. 7C schematically represents a curved head unit, all according to embodiments of the invention.

FIG. 7C shows in perspective view the distal end of retractor 10, including (truncated) shaft 26 adjoining head unit 22, according to another embodiment of the invention. A rigid or somewhat flexible shaft 26 may be preformed in the form of a curve. The total extent and rate of curvature of shaft 26 may vary according to particular intended applications of retractor 10. Similarly, head unit 22 may be curved to a greater or lesser extent, also according to the intended applications of retractor 10. For example, in the embodiment illustrated in FIG. 7C, the combined curvature of shaft 26 and head 22 is approximately 90°. However, greater or lesser amounts of curvature are contemplated for other embodiments of the invention, from a few degrees or less to 360° or more. In addition, curvature of shaft 26 and/or head unit 22 in more than one plane (not shown) is also contemplated. Such curved embodiments of retractor 10 are within the scope of the instant invention.

Figure 8A:
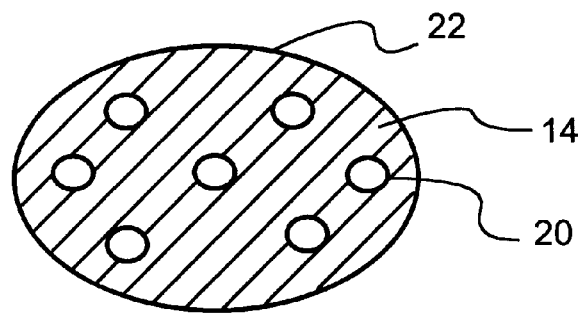
FIGS. 8A and 8B, respectively show oval and elliptical shaped end-pieces of a surgical retractor, according to the invention.
Figure 8B:
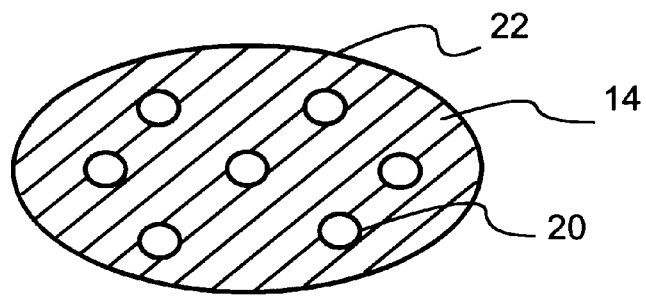

Head unit 22, which may be generally cylindrical, rounded, frusto-conical, or have other shapes as described hereinabove, may be bent or flattened over at least part of its length. Such bending or flattening of head unit 22 may be performed in a predefined manner to provide a specific shape to head distal end 22' and, concomitantly, to end-piece 14, the latter being thus adapted for retraction of particular tissues or organs. For example, FIG. 8A shows an oval or egg-shaped end-piece 14, while FIG. 8B shows an elongated oval or elliptical shaped end-piece 14, both according to the instant invention.

Figure 9A:
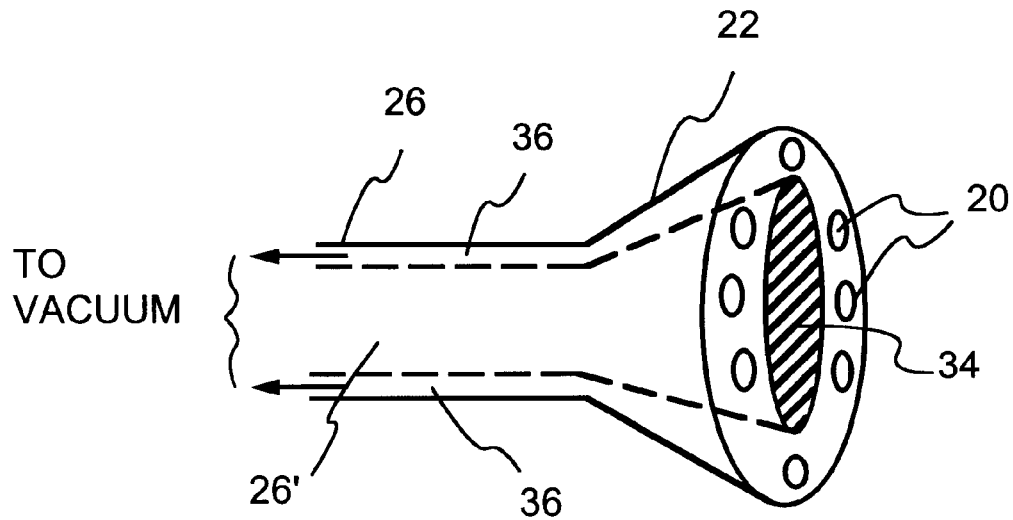
FIG. 9A is a perspective view of a head unit and (truncated) shaft of a surgical retractor including an instrument port, according to another embodiment of the invention.
Figure 9B:
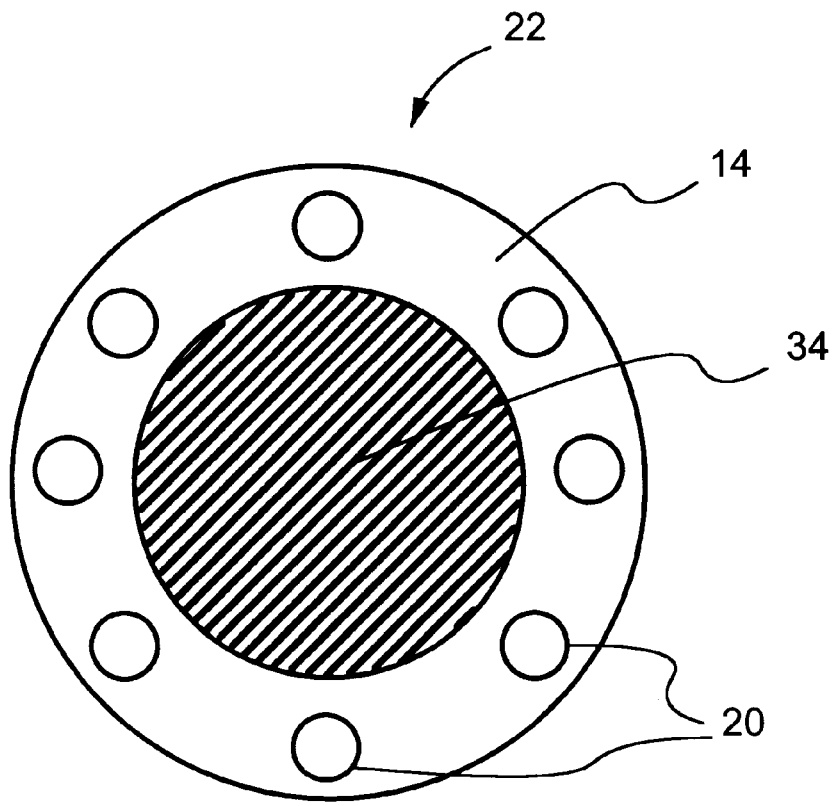
FIG. 9B is a face view of an end-piece of the head unit of FIG. 9A, according to the invention.
Figure 9C:
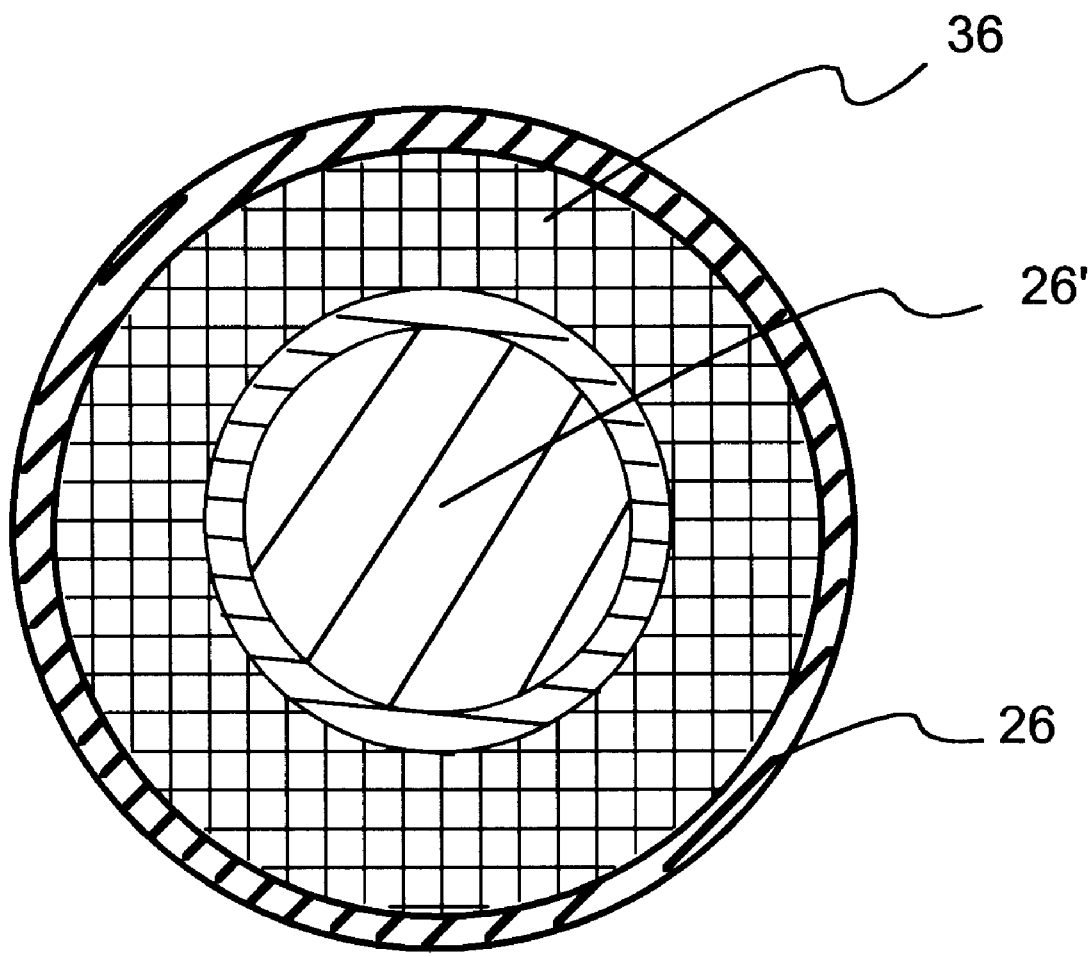
FIG. 9C is a sectional view of the shaft shown in FIG. 9A, according to another embodiment of the invention.
Figure 12A:
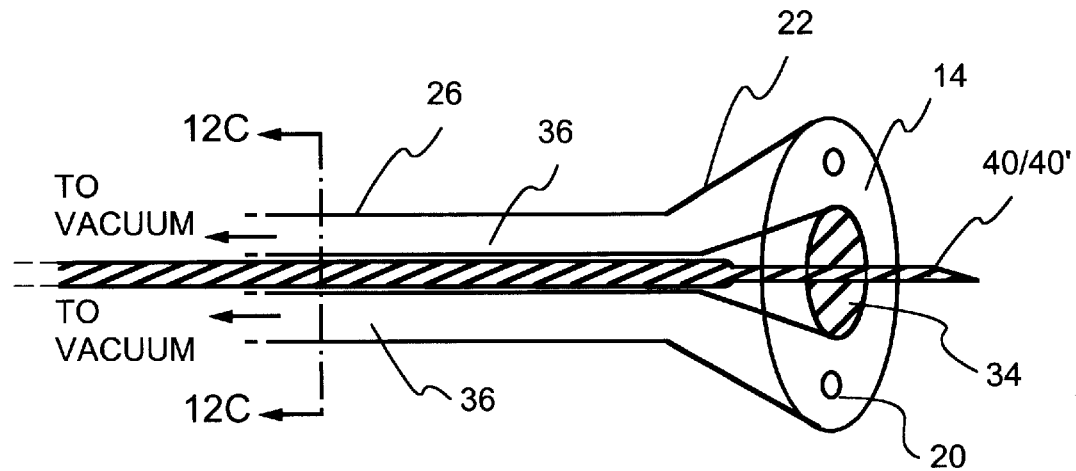
FIG. 12A shows in perspective a section of a head unit of a surgical retractor with a surgical instrument protruding from an instrument port in the end-piece of the head unit, according to another embodiment of the invention.

According to another embodiment of the invention, retractor 10 may include an instrument port 34. FIG. 9A shows a perspective view of (truncated) shaft 26 and head unit 22, including instrument port 34 in end-piece 14; and FIG. 9B shows a face view of end-piece 14 shown in FIG. 9A. Port 34 may be located substantially centrally within end-piece 14. One or more suction ports 20 may be arranged peripherally on end-piece 14. Suction ports 20 may be in communication with vacuum line 36. With reference to FIG. 9C, vacuum line 36 may be arranged peripherally within shaft 26, leaving bore 26' free for the passage of a surgical instrument or other tool (FIG. 12A). Instrument port 34 may be free of suction, or may be connected to a vacuum line (not shown) other than line 36 for aspiration of tissue and/or fluids, e.g., during biopsy.

Figure 10A:
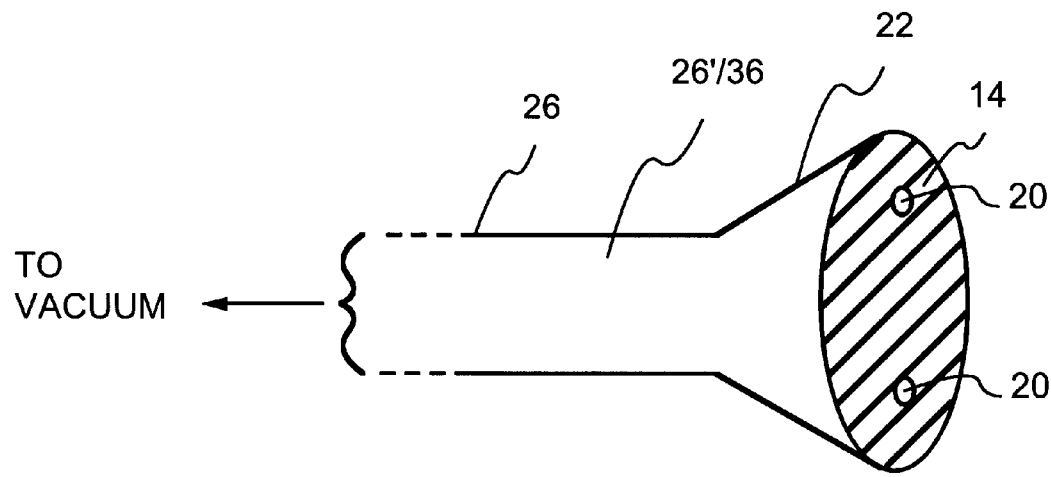
FIG. 10A is a perspective side view of a head unit and truncated shaft of a retractor, wherein a plurality of suction ports share a common vacuum line, according to one embodiment of the invention.

FIG. 10A shows head unit 22 and truncated shaft 26 of retractor 10, according to one embodiment of the instant invention, wherein a plurality of suction ports 20 share a common vacuum line 36. In this embodiment, vacuum line 36 comprises bore 26' in shaft 26.

Figure 10B:
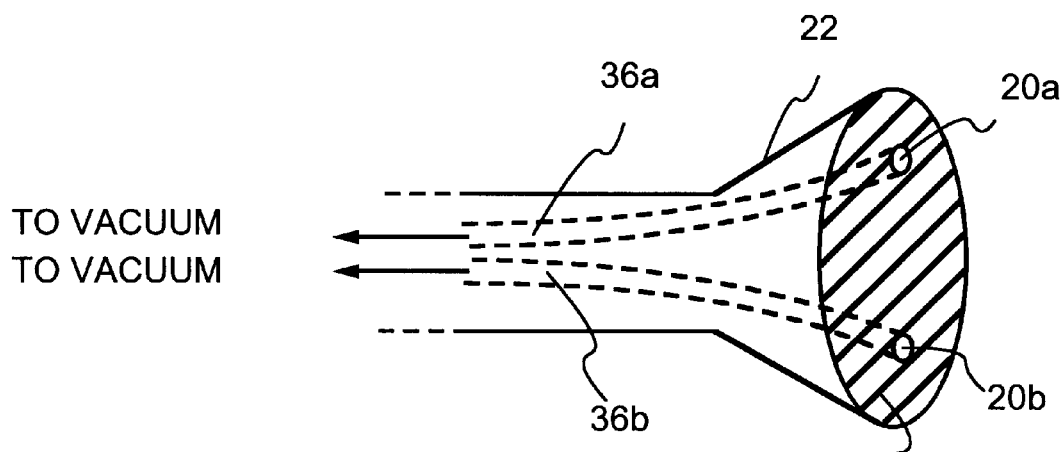
FIG. 10B is a perspective side view of a head unit and truncated shaft of a retractor, wherein a plurality of suction ports each have a dedicated vacuum line, according to another embodiment of the invention.

According to another embodiment of the instant invention, as represented in FIG. 10B, a first suction port 20a is in communication with vacuum line 36a, while a second suction port 20b is in communication with vacuum line 36b. Thus, according to the invention, each of a plurality of suction ports 20a–x may have a corresponding (dedicated) vacuum line 36a–x.

Figure 11A:
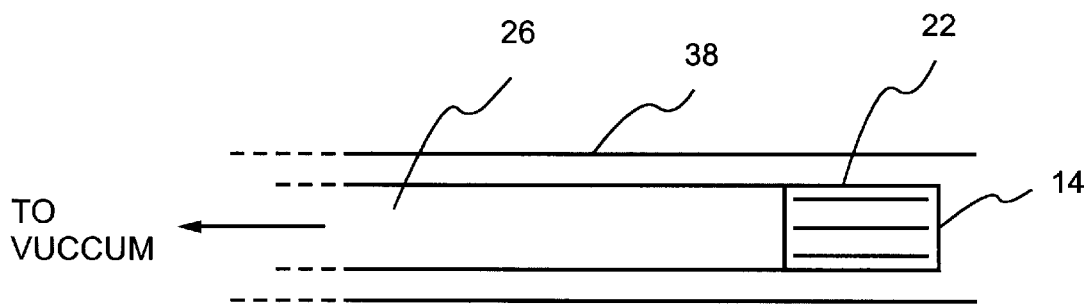
FIG. 11A is a sectional view of a head unit of a surgical retractor within a catheter showing the head unit in a folded configuration, according to another embodiment of the invention.

FIG. 11A shows the distal portion of retractor 10 including shaft 26 and head unit 22 entirely within a sheath catheter 38, for advancement of head unit 22 to an organ or body tissue to be retracted during an endoscopic procedure, according to the invention. Head unit 22 may be folded to a smaller diameter to facilitate fitting and/or movement of head unit 22 within catheter 38. Head unit 22 may comprise a pliable or compressible material to facilitate folding of head unit 22. Head unit 22 may be moved within catheter 38 using various techniques or procedures well known in the art.

Figure 11B:
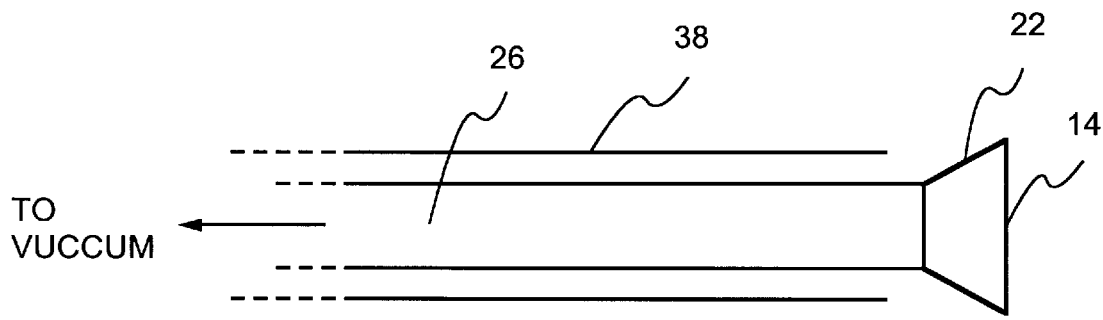
FIG. 11B is a sectional view of a surgical retractor and a catheter, showing the head unit in an erect configuration, according to the invention.

FIG. 11B shows head unit 22 protruding from catheter 38, the former in an erect or unfolded configuration. Head unit 22 may comprise one or more resilient or elastic components which allow head unit 22 to spontaneously erect when released from the physical confines of catheter 38; or, according to an alternative embodiment, head unit 22 may be erected manually by an operator of retractor 10 using techniques well known in the art.

Figure 12B:
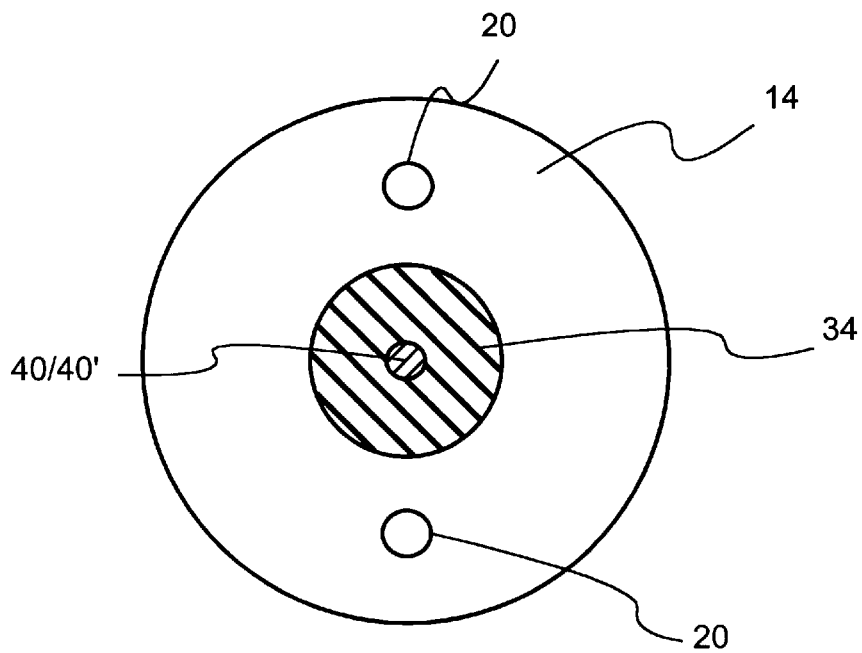
FIG. 12B is a face view of the end-piece and instrument port shown in FIG. 12A, according to the invention.
Figure 12C:
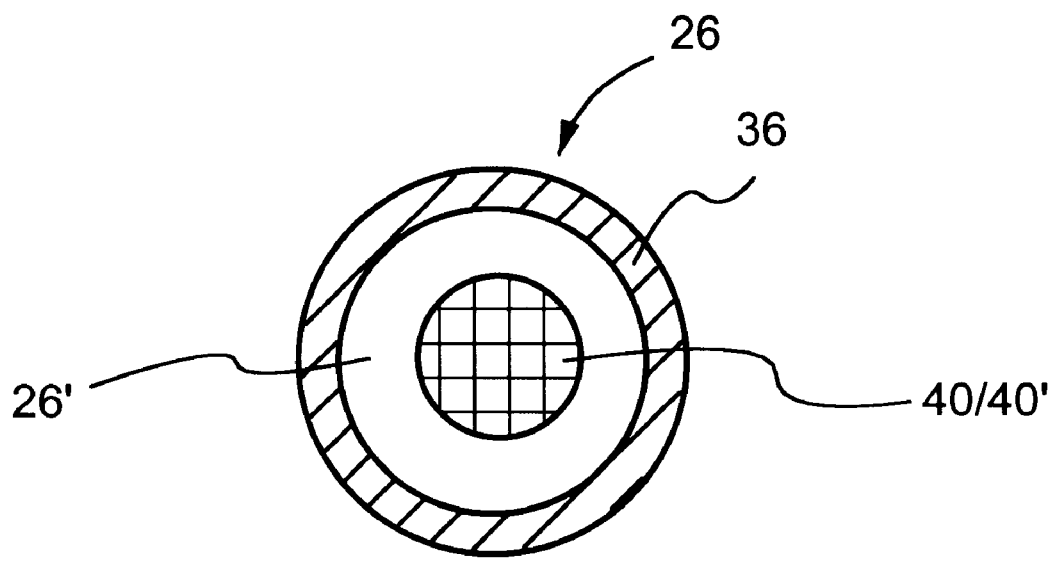
FIG. 12C shows a section of the shaft of in FIG. 12A, according to the invention.

FIG. 12A shows head unit 22 of surgical retractor 10 with a surgical instrument 40 protruding from instrument port 34, according to another embodiment of the invention. Instrument 40 may be moved longitudinally with respect to head unit 22 and end-piece 14. FIG. 12B is a face view of end-piece 14 shown in FIG. 12A. FIG. 12C is a sectional view of shaft 26 showing instrument 40 within bore 26'. Instrument 40 may comprise, for example, various types of drug delivery or tissue sampling devices. According to a currently preferred embodiment of the invention, instrument 40 comprises a tissue extraction unit 40'. Tissue extraction unit 40' may be, for example, a tissue excision or tissue sampling instrument, such as an electro-cauterization device, biopsy needle, etc. Retractor 10 having instrument port 34 and tissue extraction unit 40' may be used for conveniently retracting and sampling or excising a tumor or other tissue using a single, multi-functional apparatus. Or, where instrument 40 comprises a drug delivery device, retractor 10 having instrument port 34 may be used for the simultaneous retraction of a tumor and the application of a chemotherapeutic agent thereto.

Figure 13A:
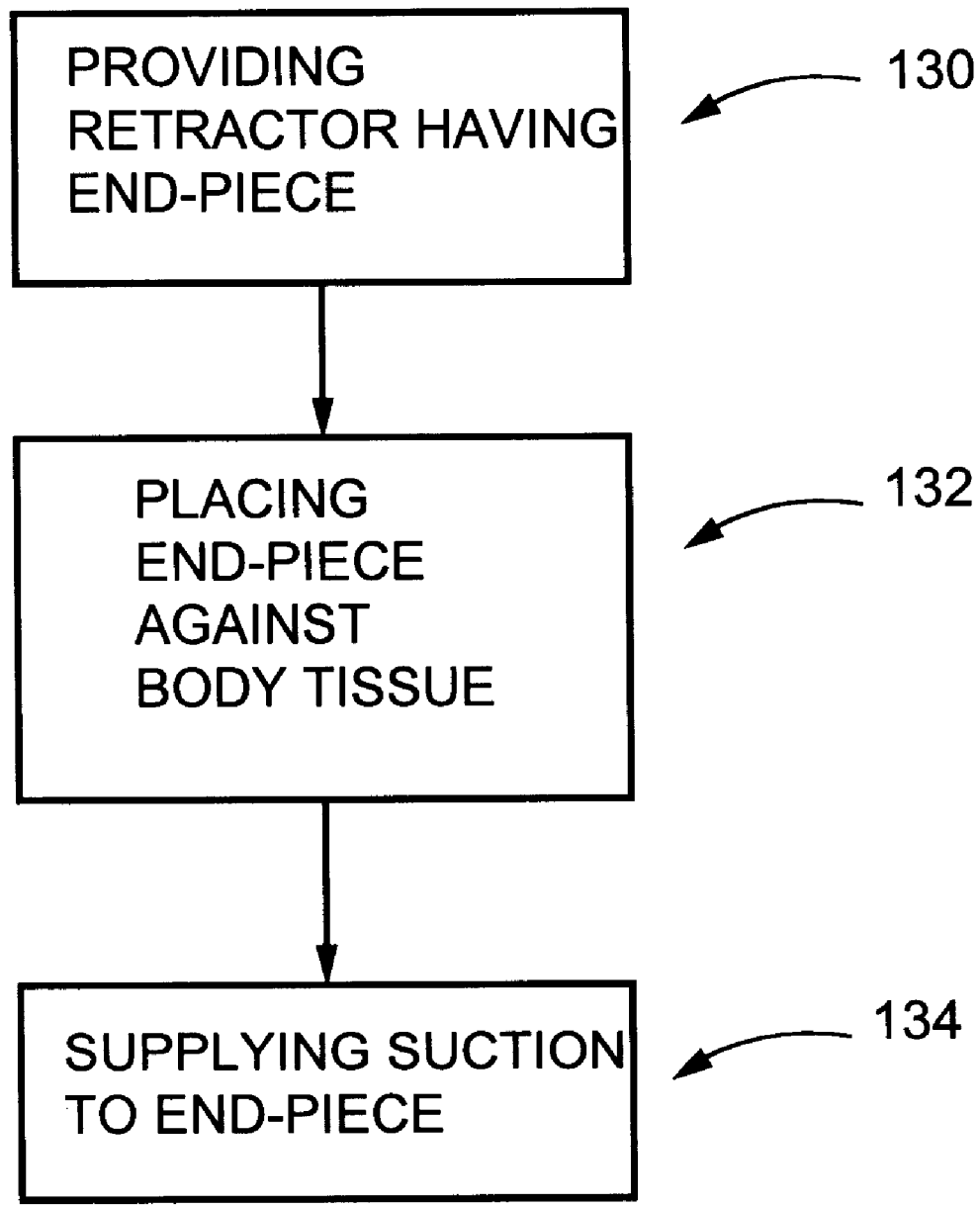
FIG. 13A schematically represents a series of steps involved in a method for retracting body tissue of a patient, according to another embodiment of the invention.
Figure 13B:
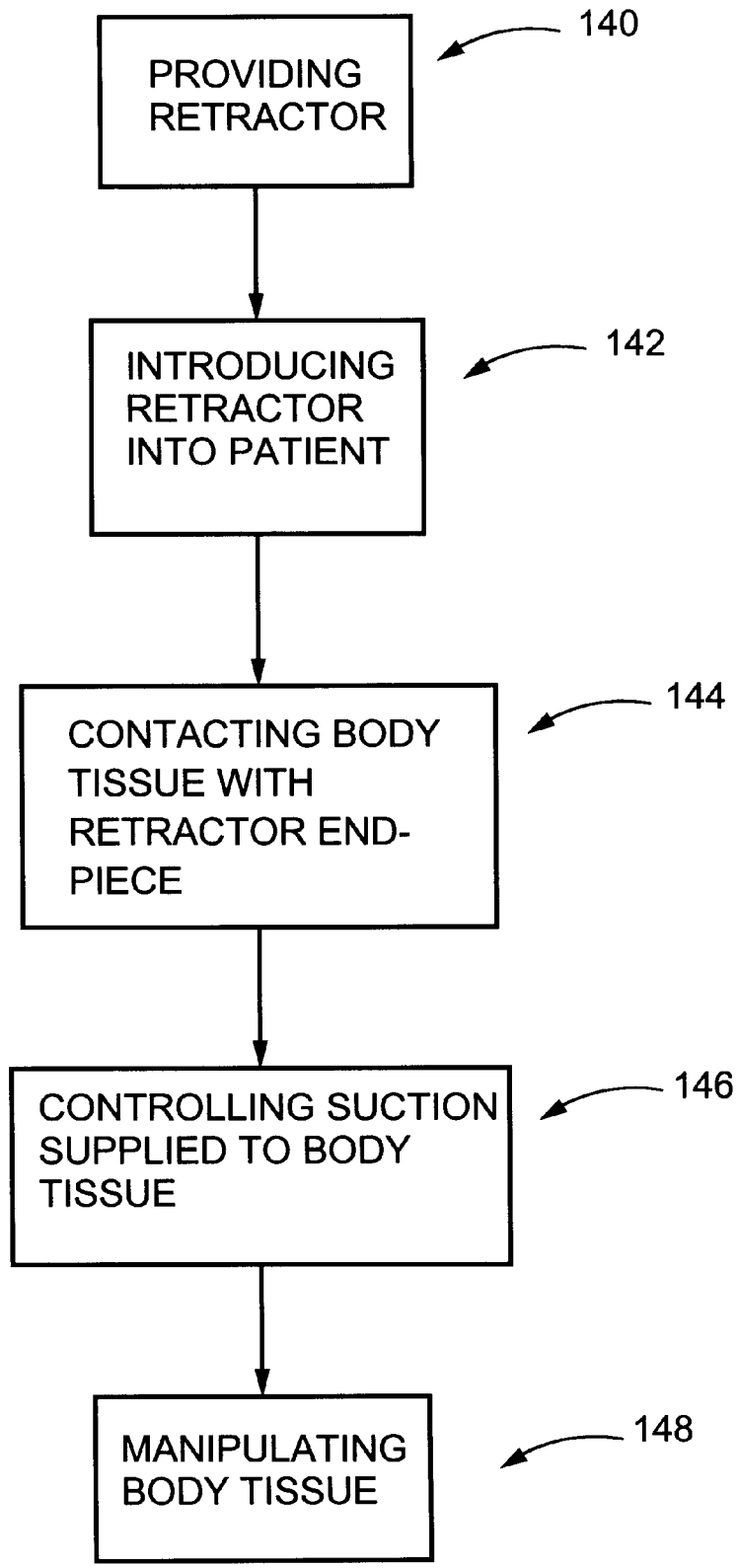
FIG. 13B schematically represents a series of steps involved in a method for retracting body tissue, according to another embodiment of the invention.

FIG. 13B schematically represents a series of steps involved in a method for retracting body tissue of a patient, according to another embodiment of the invention, wherein step 130 involves providing a vacuum actuated retractor having an end-piece. According to a currently preferred embodiment, the end-piece is attached to the head unit at or near the distal end of the head unit, the head unit being joined to a shaft. According to an alternative embodiment, the end-piece may be attached directly to a shaft, and a head unit may be omitted. Step 132 involves placing the end-piece against body tissue, such as a tumor or normal organ. Step 134 involves supplying suction to the end-piece. Specifically, suction is supplied to one or more suction ports within the end-piece. Depending on the particular application, the preference of the surgeon, an perhaps other factors, suction may be supplied to the end-piece in step 134 before, during, or after the end-piece has been placed against the target body tissue in step 132.

FIG. 13B schematically represents a series of steps involved in a method for retracting body tissue, according to another embodiment of the invention, wherein step 140 involves providing a vacuum actuated surgical retractor. Step 142 involves introducing the retractor into the patient. As an example, the retractor may be introduced into the patient via a cannula, via a catheter, a body orifice, or directly through an incision. Step 144 involves contacting body tissue, an organ, or object to be retracted with the end-piece of the retractor. Contacting of the target organ or tissue by the end-piece may be facilitated by use of video or a television lens, affixed to the retractor, and in communication with a monitor for viewing the target tissue or organ, such techniques being well known in the art.

Step 146 involves controlling suction supplied to the target tissue or organ via the end-piece. More specifically the suctional force applied to the target tissue or organ by the end-piece may be controlled qualitatively and/or quantitatively by means of a suitable vacuum control unit. A vacuum control unit may be integral with the retractor, or may be somewhat remote from the retractor, and may be operated by a hand or a foot of the surgeon. After a suitable suctional force has been applied to the target tissue or organ, step 148 involves manipulating the tissue or organ. For example, manipulating the tissue or organ may comprise mere movement of the retractor in a given direction by the surgeon's hand, and correspondingly, movement of the tissue or organ to which the retractor is suctionally attached. Alternatively (or in addition), during manipulating step 148, at least a sample of the target tissue or organ may be excised by an instrument manipulated via an instrument port located in the end-piece of the retractor (as described hereinabove with reference to FIG. 12A), or the target tissue or organ may be treated with a therapeutic agent (e.g., a drug, an antimicrobial agent, etc.).

Figure 14:
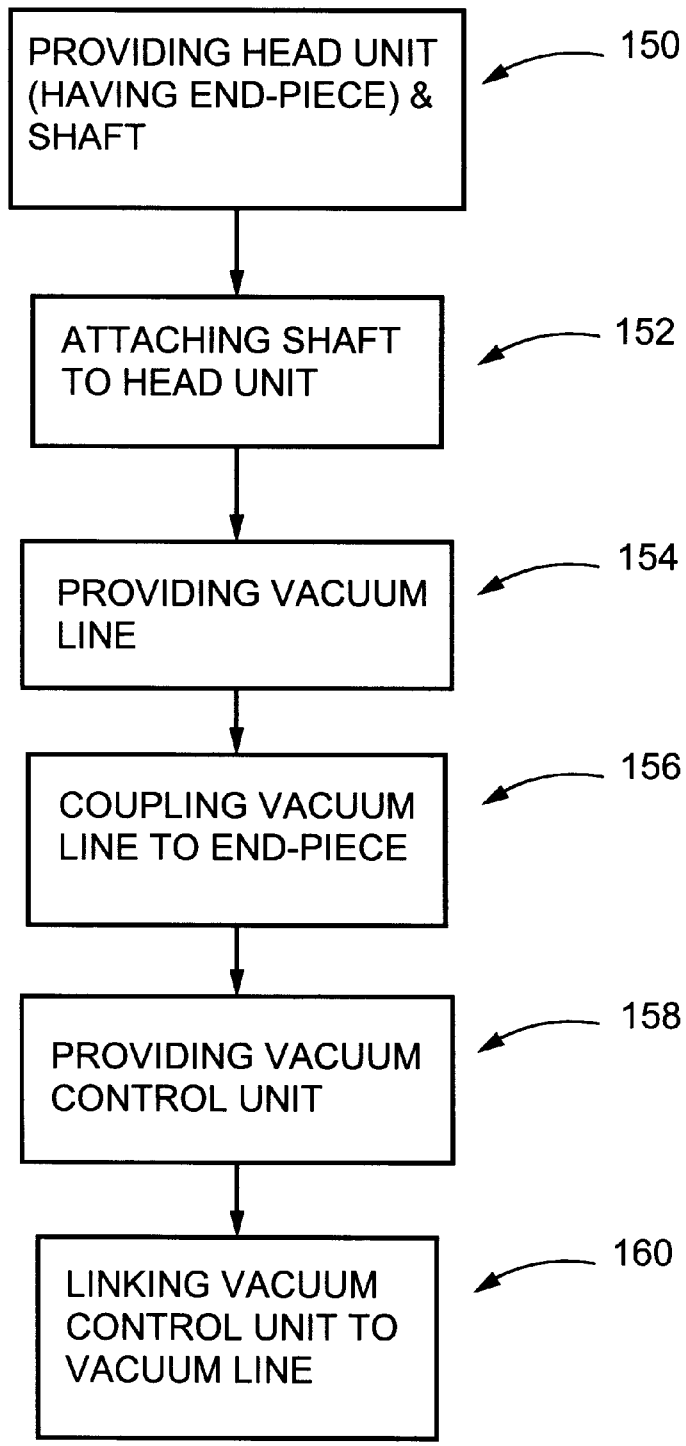
FIG. 14 schematically represents a series of steps involved in a method for making a surgical retractor, according to another embodiment of the invention.

FIG. 14 schematically represents a series of steps involved in a method for making a vacuum actuated surgical retractor, according to another embodiment of the invention, in which step 150 involves providing a shaft and a head unit, the latter having an end-piece attached at its distal end. Step 152 involves attaching a shaft to the proximal end of the head unit. The shaft may have a bore therethrough. Step 154 involves providing at least one vacuum line. According to one embodiment, a bore through the shaft may comprise the vacuum line. Step 156 involves operably coupling the at least one vacuum line to the end-piece. Step 158 involves providing at least one vacuum control unit. Step 160 involves linking the vacuum control unit to the at least one vacuum line. According to one embodiment, the vacuum control unit may be affixed to the head unit or to the shaft.

Figure 15:
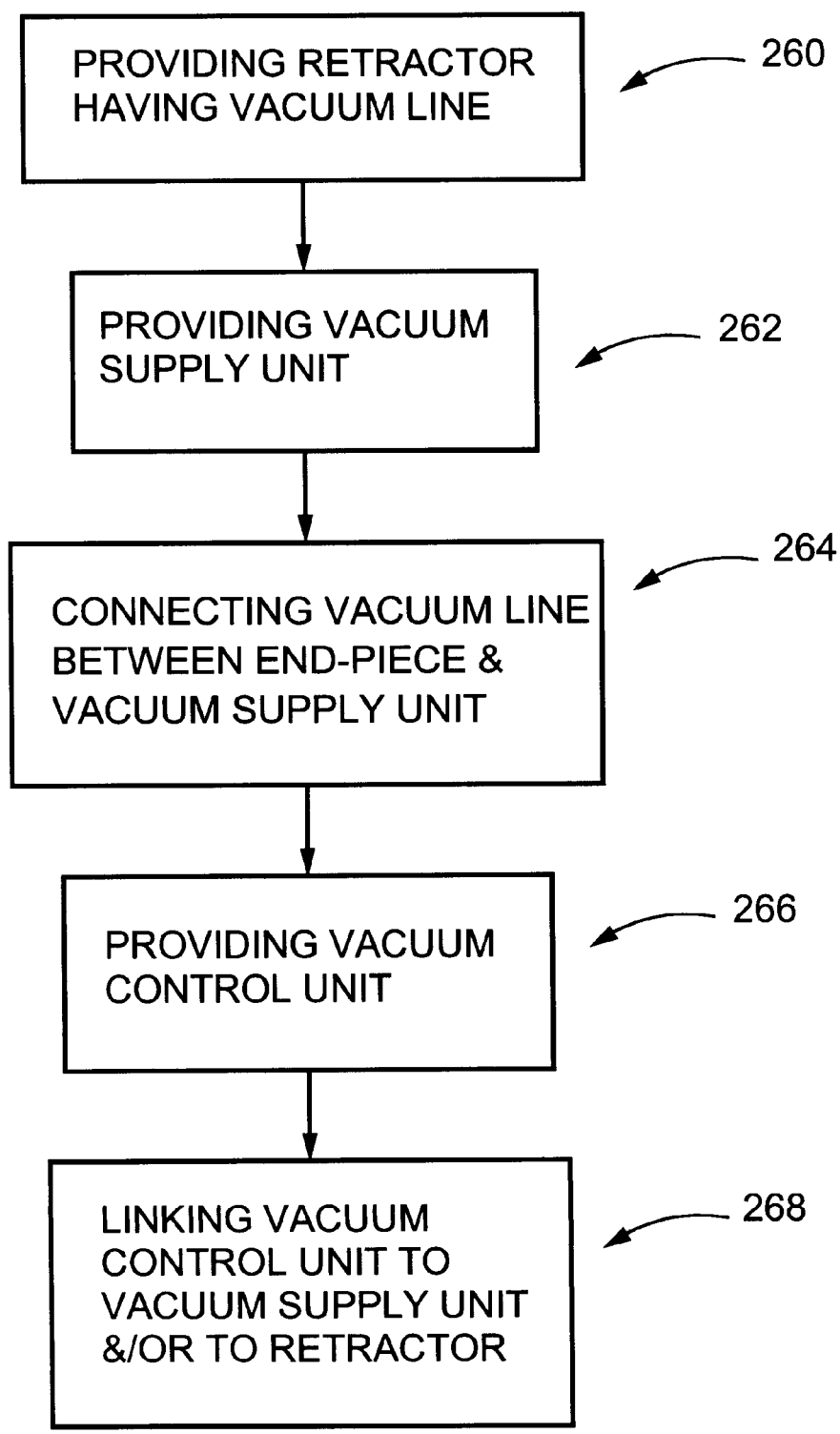
FIG. 15 schematically represents a series of steps involved in a method for making a retractor system, according to another embodiment of the invention.

FIG. 15 schematically represents a series of steps involved in a method for making a retractor system, according to another embodiment of the invention, in which step 260 involves providing a vacuum actuated surgical retractor having at least one vacuum line. The retractor includes an end-piece having at least one suction port therein, wherein the at least one suction port is adapted for making sealing engagement or contact with an organ or tissue when suction is supplied to the at least one suction port. Step 262 involves providing a vacuum supply unit for supplying a vacuum or suction to the end-piece of the retractor. Step 264 involves connecting at least one vacuum line between the end-piece and the vacuum supply unit. Step 266 involves providing at least one vacuum control unit for controlling, qualitatively and/or quantitatively, the suction supplied to the at least one suction port. Step 268 involves operably linking the at least one vacuum control unit to the vacuum supply unit and/or to the retractor. As an example, step 268 may involve coupling a vacuum control unit comprising a valve to the at least one vacuum line of the retractor as a means to control suction supplied to the at least one suction port of the end-piece.

Although the surgical retractor of the instant invention has been described herein primarily with respect to retracting an organ, tumor, or other body tissue, the invention may also be used to retrieve a foreign object introduced inadvertently, or otherwise, into the body of an individual or into a body cavity, e.g., the mouth, throat, or rectum. The apparatus and methods of the instant invention may additionally find applications in veterinary medicine.

The foregoing embodiments are merely exemplary and are not to be construed as limiting the present invention. The present teaching may be applied to other types of apparatuses and methods. The description of the present invention is intended to be illustrative, and not to limit the scope of the appended claims. Many alternatives, modifications, and variations will be apparent to those skilled in the art.

What is claimed is:

1. A vacuum actuated surgical retractor for retracting body tissue, comprising: an end-piece having at least one suction port therein, said end-piece in communication with at least one vacuum line said at least one vacuum line for supplying suction to said at least one suction port, said end-piece adapted for sealing engagement with body tissue, wherein said end-piece is capable of interconversion between a convex shape and a concave shape.

2. The retractor of claim 1, further comprising a head unit and a body portion attached to said head unit, said body portion housing said at least one vacuum line.

3. The retractor of claim 2, further comprising a shaft having a bore therethrough, said shaft connected to the proximal end of said head unit.

4. The retractor of claim 2, further comprising a sheath catheter adapted for ensheathing said head unit, said head unit movable longitudinally within said sheath catheter.

5. The retractor of claim 4, wherein said head unit is adapted to adopt a folded configuration within said sheath catheter and to adopt an erect configuration outside said sheath catheter.

6. The retractor of claim 2, wherein said head unit includes a head distal end, and said end-piece is attached to said head unit at said head distal end.

7. The retractor of claim 6, wherein said end-piece is selected from the group consisting of convex, concave, and plane, with respect to said head distal end.

8. The retractor of claim 6, wherein said end-piece is capable of interconversion between convex and concave with respect to said head distal end.

9. The retractor of claim 2, wherein said head unit includes at least one head support unit.

10. The retractor of claim 2, wherein said head unit is substantially frusto-conical in shape.

11. The retractor of claim 2, further comprising a vacuum control unit in communication with said at least one vacuum line, said vacuum control unit integral with said body portion or said head unit.

12. The surgical retractor of claim 2 further comprising a flexible neck connected to said head unit.

13. The retractor of claim 1, wherein said at least one suction port comprises a plurality of suction ports.

14. The retractor of claim 13, wherein said at least one vacuum line comprises a plurality of vacuum lines, and each of said plurality of suction ports is connected to a corresponding one of said plurality of vacuum lines.

15. The retractor of claim 13, wherein said plurality of suction ports are connected to a single vacuum line.

16. The retractor of claim 1, wherein said end-piece includes an instrument port.

17. The retractor of claim 16, further comprising a tissue extraction unit, and wherein said instrument port is adapted to accommodate said tissue extraction unit.

18. The retractor of claim 1, wherein said end-piece includes an end-piece auxiliary sealing unit.

19. The retractor of claim 1, wherein said end-piece comprises a pliable material adapted to conform to a surface of body tissue over at least part of the area of said end-piece upon contact of the at least part of the area of said end-piece with the surface of body tissue.

20. The retractor of claim 1, wherein said end-piece comprises a material selected from the group consisting of silicone rubber, latex and, neoprene.

21. A vacuum actuated surgical retractor system for retraction of body tissue, comprising:
a) a retractor including an end-piece, said end-piece adapted for sealing engagement against body tissue, wherein said end-piece is capable of interconversion between a convex shape and a concave shape, said end-piece including at least one suction port, said at least one suction port for exerting a suction force on the body tissue;
b) a vacuum supply unit operably linked to said end-piece, said vacuum supply unit for supplying suction to said at least one suction port; and
c) a vacuum control unit for controlling suction to said at least one suction port.

22. The system of claim 21, wherein said retractor further comprises a body portion including a shaft having a bore therethrough, said bore connected to said vacuum supply unit, said body portion attached to a head unit having a head distal end, said end-piece sealingly attached to said head unit at said head distal end.

23. The system of claim 21, wherein said vacuum control unit is adapted for controlling the magnitude of the suction force exerted on the body tissue.

24. The system of claim 21, wherein said vacuum control unit is adapted for turning on and off the suction supplied to said at least one suction port.

25. The system of claim 21, wherein said vacuum control unit is integral with said retractor.

26. The system of claim 21, wherein said vacuum control unit comprises a valve.

27. The system of claim 21, wherein said vacuum control unit is remote from said retractor.

28. The system of claim 27, wherein said vacuum control unit is foot operated.

29. A method of atraumatically retracting body tissue with a vacuum actuated surgical retractor, comprising the steps of:
a) placing an end-piece of the surgical retractor against body tissue to be retracted, wherein said end-piece is capable of interconversion between a convex shape and a concave shape, the end-piece having at least one suction port; and
b) supplying suction to the at least one suction port such that a suction force is exerted on the body tissue via the end-piece.

30. The method of claim 29, further comprising the step of:
c) after said step b), manipulating the body tissue to which suction is supplied in said step b).

31. The method of claim 30, wherein said step c) comprises excising at least a portion of the body tissue retracted.

32. The method of claim 29, wherein said step c) comprises treating the body tissue to be retracted with a therapeutic agent.

33. The method of claim 29, wherein said step a) comprises endoscopically advancing the retractor towards the body tissue to be retracted.

34. The method of claim 29, wherein said step b) comprises supplying suction to the at least one suction port via a vacuum supply unit.

35. The method of claim 29, further comprising the step of:
   d) controlling the suction force exerted on the body tissue via a vacuum control unit.

36. A method of making a surgical retractor, comprising the steps of:
   a) providing a head unit having an end-piece sealingly attached to a distal end of the head unit, wherein said end-piece is capable of interconversion between a convex shape and a concave shape, the end-piece having at least one suction port therein;
   b) providing at least one vacuum line; and
   c) operably coupling the at least one vacuum line to the end-piece.

37. The method of claim 36, further comprising the step of attaching a shaft to the proximal end of the head unit, the shaft having a bore therethrough, the bore comprising the at least one vacuum line.

38. The method of claim 36, further comprising the step of providing a vacuum control unit for controlling suction at the at least one suction port.

39. A method for making a vacuum actuated surgical retractor system, comprising the steps of:
   a) providing a surgical retractor having an end-piece capable of interconversion between a convex shape and a concave shape, at least one suction port in the end-piece, and at least one vacuum line;
   b) providing a vacuum supply unit;
   c) connecting the at least one vacuum line to the vacuum supply unit;
   d) providing at least one vacuum control unit; and
   e) operably linking the at least one vacuum control unit to the vacuum supply unit or to the retractor.

40. The method of claim 39, wherein said step d) comprises providing a foot operated vacuum control unit.

41. The method of claim 39, wherein said step e) comprises operably linking the at least one vacuum control unit to the at least one vacuum line of the retractor.

42. The method of claim 41, wherein said step e) comprises affixing the vacuum control unit to the retractor.

43. The method of claim 41, wherein said step d) comprises providing a vacuum control unit including a valve.

44. A vacuum actuated surgical retractor for retracting body tissue, comprising:
   a) a shaft;
   b) a neck portion connected to the shaft, wherein a material comprising said neck portion possesses positional memory;
   c) a head unit connected to the neck, the head unit including an end-piece having at least one suction port therein, said end-piece being in communication with at least one vacuum line said at least one vacuum line for supplying suction to said at least one suction port, said end-piece adapted for sealing engagement with body tissue.

45. The retractor of claim 44 wherein the shaft includes a flexible tapering portion and a spring disposed within the tapering portion.

* * * * *